(12) United States Patent
Gerbec et al.

(10) Patent No.: US 6,902,583 B2
(45) Date of Patent: Jun. 7, 2005

(54) TRIPARTITE ATTACHMENT MECHANISM AND METHOD FOR A MODULAR PROSTHESIS

(75) Inventors: Daniel E. Gerbec, Logan, UT (US); T. Wade Fallin, Hyde Park, UT (US)

(73) Assignee: MedicineLodge, Inc., Logan, UT (US)

( * ) Notice: Subject to any disclaimer, the term of this patent is extended or adjusted under 35 U.S.C. 154(b) by 136 days.

(21) Appl. No.: 10/132,669

(22) Filed: Apr. 25, 2002

(65) Prior Publication Data

US 2003/0204269 A1 Oct. 30, 2003

(51) Int. Cl.$^7$ ................................................ A81F 2/28
(52) U.S. Cl. ..................................................... 623/23.47
(58) Field of Search ................. 623/22.11, 23.11–23.38

(56) References Cited

U.S. PATENT DOCUMENTS

| | | | |
|---|---|---|---|
| 2,682,265 A | 6/1954 | Collison | |
| 2,785,673 A | 3/1957 | Anderson | |
| 3,806,957 A | 4/1974 | Shersher | |
| 3,848,272 A | 11/1974 | Noiles | |
| 3,875,593 A | 4/1975 | Shersher | |
| 3,906,550 A | 9/1975 | Rostoker et al. | |
| 3,943,576 A | 3/1976 | Sivash | |
| 3,987,499 A | 10/1976 | Scharback et al. | |
| 4,016,651 A | 4/1977 | Kawahara et al. | |
| 4,051,559 A | 10/1977 | Pifferi | |
| 4,086,701 A | 5/1978 | Kawahara et al. | |
| 4,259,072 A | 3/1981 | Hirabayashi et al. | |
| 4,304,011 A | 12/1981 | Whelam, III | |
| 4,404,691 A | 9/1983 | Buning et al. | |
| 4,520,511 A | 6/1985 | Gianezio et al. | |
| 4,578,081 A | 3/1986 | Harder et al. | |
| 4,619,659 A | 10/1986 | Witzel | |
| 4,624,673 A | 11/1986 | Meyer | |
| 4,676,797 A | 6/1987 | Anapliotis et al. | |
| 4,714,471 A | 12/1987 | Grundei | |
| 4,790,854 A | 12/1988 | Harder et al. | |
| 4,822,366 A | 4/1989 | Bolesky | |
| 4,842,606 A | 6/1989 | Kranz et al. | |
| 4,846,839 A | 7/1989 | Noiles | |
| 4,851,007 A | 7/1989 | Gray | |
| 4,878,917 A | * 11/1989 | Kranz et al. | 623/23.45 |
| 4,908,032 A | 3/1990 | Keller | |
| 4,917,530 A | 4/1990 | Engelhardt et al. | |
| 4,919,678 A | 4/1990 | Kranz | |
| 4,936,853 A | 6/1990 | Fabian et al. | |
| 4,938,773 A | 7/1990 | Strand | |
| 4,985,037 A | 1/1991 | Petersen | |
| 4,995,883 A | 2/1991 | Demane et al. | |
| 5,002,578 A | 3/1991 | Luman | |
| 5,002,581 A | 3/1991 | Paxson et al. | |

(Continued)

FOREIGN PATENT DOCUMENTS

| | | |
|---|---|---|
| DE | 32 05 577 A1 | 10/1982 |
| DE | 33 40 767 A1 | 5/1985 |
| DE | 40 31 520 A1 | 4/1992 |

(Continued)

*Primary Examiner*—Kevin Shaver
*Assistant Examiner*—Michael B. Priddy
(74) *Attorney, Agent, or Firm*—Workman Nydegger

(57) ABSTRACT

A tripartite attachment mechanism for a modular prosthesis comprises a body, a sleeve and a shaft. The body has a top end, a bottom end, an internal surface bounding a bore extending between the top and bottom ends, and an external prosthetic surface. The sleeve has a channel extending therethrough, an external prosthetic surface, and a protrusion having an outer surface adapted to be received in the bore. The shaft is adapted to be slidingly received in the bore and the channel. With the shaft in the bore and the channel, sliding the protrusion into the bore causes the internal surface of the bore to bias against the external surface of the protrusion and further causes the internal surface of the channel to bias against the shaft, thereby locking the body, sleeve, and stem in a fixed relative position.

25 Claims, 5 Drawing Sheets

U.S. PATENT DOCUMENTS

| | | |
|---|---|---|
| 5,019,108 A | 5/1991 | Bertin et al. |
| 5,026,280 A | 6/1991 | Dürr et al. |
| 5,035,712 A | 7/1991 | Hoffman |
| 5,058,936 A | 10/1991 | Kapgan et al. |
| 5,080,676 A | 1/1992 | May |
| 5,080,685 A | 1/1992 | Bolesky et al. |
| 5,108,437 A | 4/1992 | Kenna |
| 5,108,452 A | 4/1992 | DeMane et al. |
| 5,133,760 A | 7/1992 | Petersen et al. |
| 5,133,771 A | 7/1992 | Duncan et al. |
| 5,152,796 A | 10/1992 | Slamin |
| 5,181,928 A | 1/1993 | Bolesky et al. |
| 5,190,546 A | 3/1993 | Jervis |
| 5,194,066 A | 3/1993 | Van Zile |
| 5,197,720 A | 3/1993 | Renz et al. |
| 5,201,882 A | 4/1993 | Paxson |
| 5,286,260 A | 2/1994 | Bolesky et al. |
| 5,314,479 A | 5/1994 | Rockwood, Jr. et al. |
| 5,342,366 A | 8/1994 | Whiteside et al. |
| 5,344,457 A | 9/1994 | Pilliar et al. |
| 5,370,706 A | 12/1994 | Bolesky et al. |
| 5,489,309 A | 2/1996 | Lackey et al. |
| 5,489,311 A | 2/1996 | Cipolletti |
| 5,507,817 A | 4/1996 | Craig et al. |
| 5,507,826 A | 4/1996 | Besselink et al. |
| 5,507,830 A | 4/1996 | DeMane et al. |
| 5,549,706 A | 8/1996 | McCarthy |
| 5,580,247 A | 12/1996 | Gittleman |
| 5,584,695 A | 12/1996 | Lal Sachdeva et al. |
| 5,597,378 A | 1/1997 | Jervis |
| 5,607,431 A | 3/1997 | Dudasik et al. |
| 5,609,645 A | 3/1997 | Vinciguerra |
| 5,645,607 A | 7/1997 | Hickey |
| 5,653,764 A | 8/1997 | Murphy |
| 5,653,765 A | 8/1997 | McTighe et al. |
| 5,658,349 A | 8/1997 | Brooks et al. |
| 5,665,121 A | 9/1997 | Gie et al. |
| 5,683,404 A | 11/1997 | Johnson |
| 5,702,480 A | 12/1997 | Kroph et al. |
| 5,702,486 A | 12/1997 | Craig et al. |
| 5,725,592 A | 3/1998 | White et al. |
| 5,755,720 A | 5/1998 | Mikhail |
| 5,766,262 A | 6/1998 | Mikhail |
| 5,766,263 A | 6/1998 | Grundei et al. |
| 5,776,200 A | 7/1998 | Johnson et al. |
| 5,782,921 A | 7/1998 | Colleran et al. |
| 5,791,899 A | 8/1998 | Sachdeva et al. |
| 5,858,020 A | 1/1999 | Johnson et al. |
| 5,860,982 A | 1/1999 | Ro et al. |
| 5,876,459 A | 3/1999 | Powell |
| 5,885,295 A | 3/1999 | McDaniel et al. |
| 5,888,206 A | 3/1999 | Lob et al. |
| 5,888,208 A | 3/1999 | Ro |
| 5,902,340 A | 5/1999 | White et al. |
| 5,906,644 A | 5/1999 | Powell |
| 5,931,871 A | 8/1999 | Baur et al. |
| 5,944,756 A | 8/1999 | Fischetti et al. |
| 5,954,725 A | 9/1999 | Sherman et al. |
| 5,976,147 A | 11/1999 | LaSalle et al. |
| 5,976,188 A | 11/1999 | Dextradeur et al. |
| 6,048,365 A | 4/2000 | Burrows et al. |
| 6,074,424 A | 6/2000 | Perrone, Jr. et al. |
| 6,086,614 A | 7/2000 | Mumme |
| 6,090,146 A | 7/2000 | Rozow, III et al. |
| 6,099,570 A | 8/2000 | Livet et al. |
| 6,102,956 A | 8/2000 | Kranz |
| 6,109,602 A | 8/2000 | Schron, Jr. et al. |
| 6,126,691 A | 10/2000 | Kasra et al. |
| 6,136,035 A | 10/2000 | Lob et al. |
| 6,139,584 A | 10/2000 | Ochoa et al. |
| 6,165,223 A | 12/2000 | Metzger et al. |
| 6,193,759 B1 | 2/2001 | Ro et al. |
| 6,197,063 B1 | 3/2001 | Dews |
| 6,203,575 B1 | 3/2001 | Farey |
| 6,210,413 B1 | 4/2001 | Justis et al. |
| 6,214,052 B1 | 4/2001 | Burkinshaw |
| 6,214,053 B1 | 4/2001 | Ling et al. |
| 6,238,436 B1 * | 5/2001 | Lob et al. ............... 623/22.42 |
| 6,257,593 B1 | 7/2001 | White |
| 6,264,699 B1 * | 7/2001 | Noiles et al. ............ 623/23.23 |
| 6,273,915 B1 | 8/2001 | Grimes |
| 6,290,726 B1 | 9/2001 | Pope et al. |
| 6,299,648 B1 * | 10/2001 | Doubler et al. .......... 623/23.18 |
| 6,306,174 B1 | 10/2001 | Gie et al. |
| 6,319,286 B1 | 11/2001 | Fernandez et al. |
| 6,379,388 B1 | 4/2002 | Ensign et al. |
| 6,682,568 B2 * | 1/2004 | Despres et al. .......... 623/22.42 |
| 2002/0004685 A1 | 1/2002 | White |
| 2002/0007220 A1 | 1/2002 | Gie et al. |
| 2002/0072802 A1 | 6/2002 | O'Neil et al. |
| 2002/0103541 A1 | 8/2002 | Meyers et al. |

FOREIGN PATENT DOCUMENTS

| | | |
|---|---|---|
| EP | 0 000 549 A1 | 2/1979 |
| EP | 0 201 407 A1 | 11/1986 |
| EP | 0 283 706 A1 | 9/1988 |
| EP | 0 336 774 B1 | 10/1989 |
| EP | 0 336 774 A1 | 10/1989 |
| EP | 0 359 457 A1 | 3/1990 |
| EP | 0 376 658 A2 | 7/1990 |
| EP | 0 433 121 A1 | 6/1991 |
| EP | 0 495 340 A1 | 7/1992 |
| EP | 0 556 997 A1 | 8/1993 |
| EP | 0 714 645 B1 | 6/1996 |
| EP | 0 714 645 A1 | 6/1996 |
| EP | 0 832 620 A3 | 4/1998 |
| EP | 0 878 177 A3 | 11/1998 |
| EP | 0 913 132 A1 | 5/1999 |
| EP | 1 004 283 A2 | 5/2000 |
| EP | 1 132 064 A2 | 9/2001 |
| FR | 2 225 141 | 11/1974 |
| FR | 2 705 558 | 12/1994 |
| WO | WO 83/02555 | 8/1983 |
| WO | WO 85/03426 | 8/1985 |
| WO | WO 86/02260 | 4/1986 |
| WO | WO 86/06954 | 12/1986 |
| WO | WO 91/17723 | 11/1991 |
| WO | WO 91/18563 | 12/1991 |
| WO | WO 96/13233 | 5/1996 |
| WO | WO 97/20525 | 6/1997 |
| WO | WO 98/08467 | 3/1998 |
| WO | WO 98/08468 | 3/1998 |
| WO | WO 00/72784 A1 | 12/2000 |
| WO | WO 02/07647 A2 | 1/2002 |

* cited by examiner

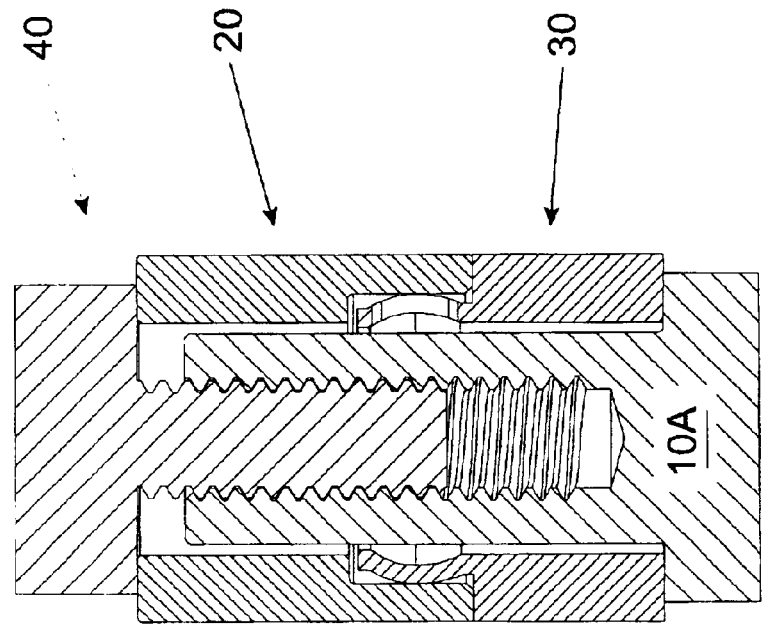
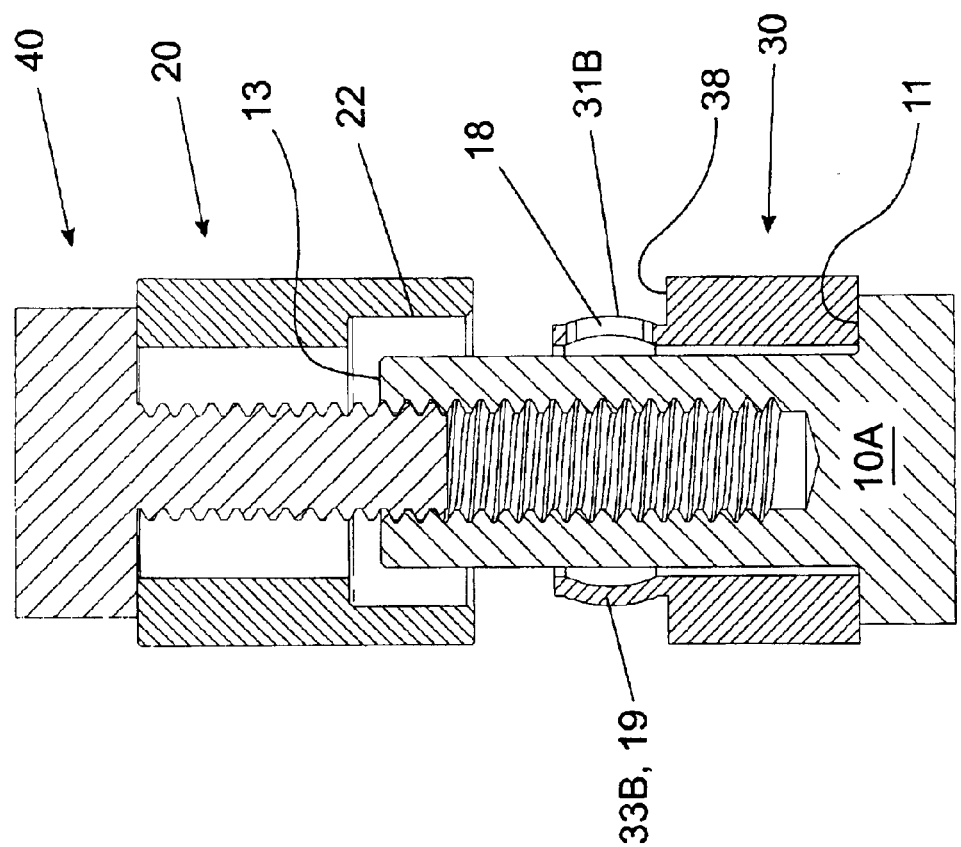
Fig. 3 A
Fig. 3 B

TRIPARTITE ATTACHMENT MECHANISM AND METHOD FOR A MODULAR PROSTHESIS

CROSS-REFERENCE TO RELATED APPLICATIONS

Not applicable.

BACKGROUND OF THE INVENTION

1. The Field of the Invention

The present invention relates generally to modular orthopedic prostheses and, more specifically, to attachment mechanisms for securing components of a modular orthopedic prosthesis.

2. The Relevant Technology

Modular orthopedic prostheses offer many advantages to the user. By selecting independent modular components to construct a complete prosthesis, custom fitting of a patient's specific anatomy or specific bony condition can be accomplished.

Several attachment mechanisms are known in the art for connecting the components of a modular prosthesis. As used herein, collet refers to a thin cylindrical tube with longitudinally extending slots, such as those commonly used in the machine tool industry. For example, it is known in the art to use an interpositional, independent collet to connect one bone contacting component of a modular prosthesis to another bone contacting component of a modular prosthesis. However, the use of the independent collet adds another component to the sum of components required to construct the complete prosthesis. It would therefore be an improvement in the art to provide an attachment mechanism that would reduce the number of components required to construct a complete prosthesis in order to reduce cost and simplify the assembly technique.

Because of the high physiological loads borne by the skeletal structure, orthopedic prostheses are subject to high bending, shear, and torsional loads. However, independent collets and other fasteners all represent adjunctive components that do provide bone contacting surfaces and therefore necessarily require a reduction in thickness of the mated bone contacting components in order to accommodate the connection hardware. Thus, the mated bone contacting components are weaker due to the reduction in thickness associated with the accommodation of the connection hardware. It would therefore be an improvement in the art to provide an attachment mechanism that integrates the means of connection between modular components of a modular prosthesis into one or more of the bone contacting components.

One of the advantages of modular orthopedic prostheses is the capacity to select, at the time of surgery, a desired orientation between modular components. Many modular connections known in the art do not facilitate a state of partial assembly that closely replicates the final longitudinal configuration of the prosthesis, where, in the state of partial assembly, the modular components can be freely rotated with respect to each other. It would therefore be another improvement in the art to provide an attachment mechanism for modular prostheses that would accommodate a state of partial assembly that closely replicates the longitudinal configuration of the prosthesis while permitting free relative rotation between the modular components.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 3A is a cross sectional view of a still another embodiment of a tripartite attachment mechanism in a disassembled state.

FIG. 3B is the tripartite attachment mechanism shown in FIG. 3A in an assembled state.

DETAILED DESCRIPTION OF THE PREFERRED EMBODIMENTS

Referring to one or more of the preferred embodiments of the present invention as depicted in FIGS. 1–5, there are three components, a body 20, a sleeve 30 and a shaft 10, adapted to connect to each other to form a tripartite, or three-piece, modular prosthesis assembly. Body 20, sleeve 30 and shaft 10 may be made from any suitable biocompatible material that can withstand the physiological loads during the lifetime of the implant. Preferentially, body 20, sleeve 30 and shaft 10 would be made from biocompatible metals, such as titanium alloys, zirconium alloys, cobalt chromium alloys, or stainless steels.

Figure 1:
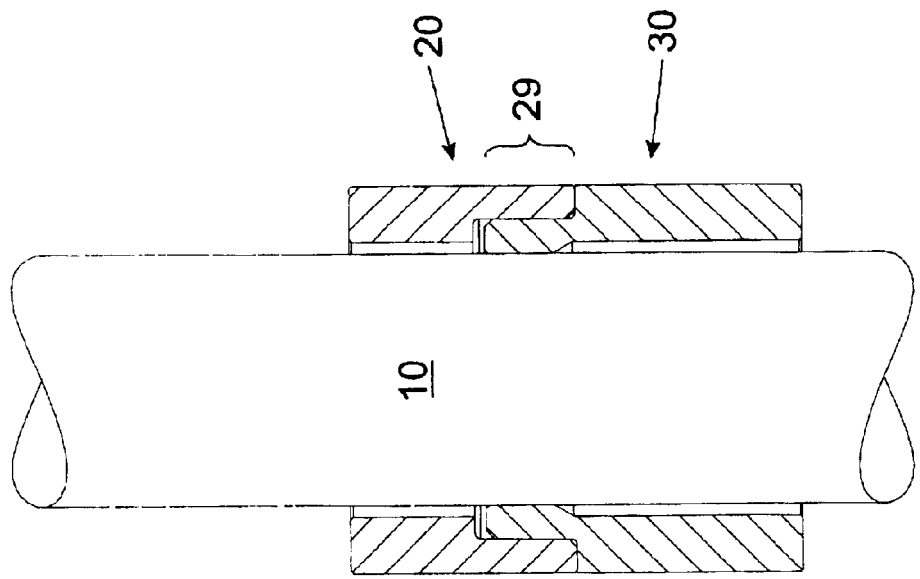
FIG. 1A is a cross sectional view of a tripartite attachment mechanism in a disassembled state.
FIG. 1B is the tripartite attachment mechanism shown in FIG. 1A in an assembled state.
Figure 1:
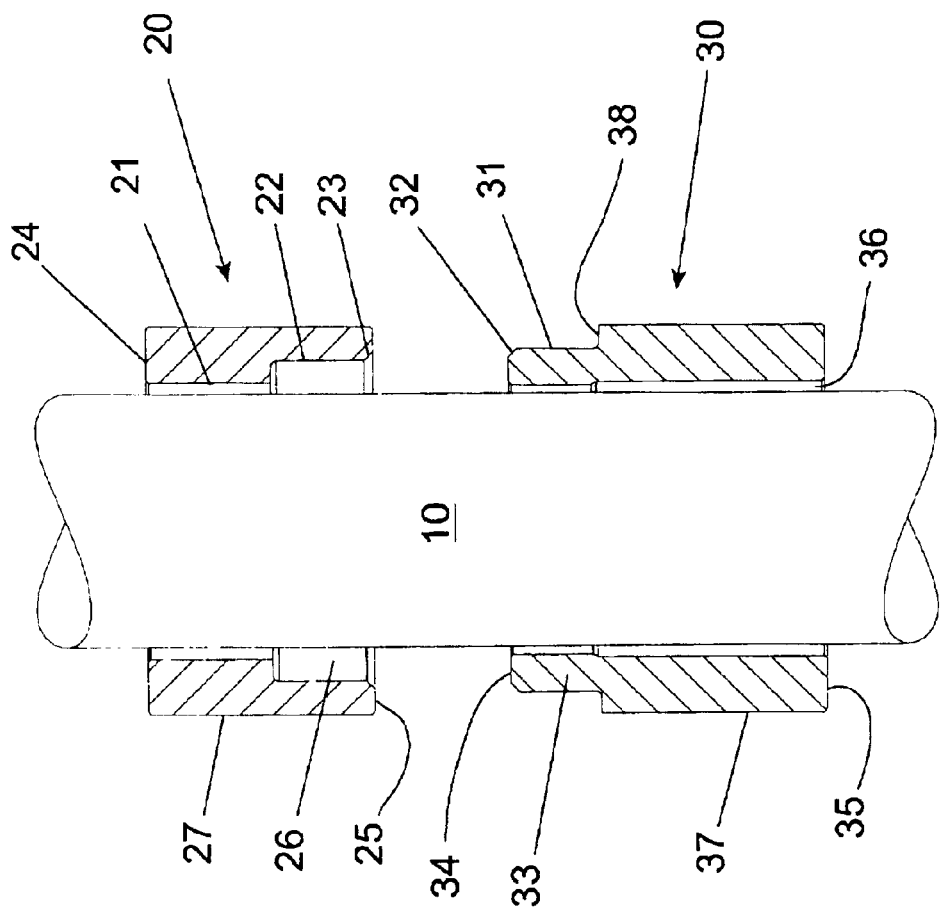

Depicted in FIG. 1 is an attachment mechanism in a disassembled state. The attachment mechanism is comprised of the body 20, the sleeve 30 and the shaft 10.

The body 20 has a first top end 24, a first bottom end 25, a first internal surface bounding a bore 22 extending between the first top end 24 and first bottom end 25. The bore 22 comprises an upper socket 21 and a longitudinally spaced lower socket 22. Additionally, the body has an external prosthetic surface 27 adapted to either contact bone or to engage either prosthetic or anatomical articulating surfaces. For simplicity, external prosthetic surface 27 is shown in FIGS. 1–4 as a cylinder, but it is appreciated that, as shown in FIGS. 5–6, the external prosthetic surfaces 27C and 27D are adapted to provide the appropriate surface for a particular prosthetic application.

The sleeve comprises a second top end 34, a shoulder 38, a second bottom end 35, a second internal surface bounding a channel 36 extending between the second top end 34 and the second bottom 35. The sleeve further has an external prosthetic surface 37 extending between the shoulder 38 and the second bottom end 35. For simplicity, external prosthetic surface 37 is shown in FIGS. 1–4 as a cylinder, but it is appreciated that, as shown in FIGS. 5–6, the external prosthetic surfaces 37C and 37D are adapted to provide the appropriate surface for a particular prosthetic application. The sleeve also has a tubular protrusion 33 extending between the shoulder 38 and the second top end 34. Additionally, the tubular protrusion has an outer surface 31.

Depicted in FIG. 1B is an assembled tripartite attachment mechanism. The lower socket 22 is sized for an interference fit with the external surface 31 of the protrusion 33. Upon assembly by compressing body 20 toward sleeve 30, the internal surface of bore 26 is biased into frictional engagement with outer surface 31 of protrusion 33. Simultaneously, the internal surface of the channel 36 is biased into frictional engagement with the shaft 10, because the protrusion 33 is elastic deflected inward toward the shaft 10 due to the interference fit between the external surface 31 and the protrusion 33. Thus, the body 20, sleeve 30, and shaft 10 are releasably locked together. By extracting sleeve 20 from body 30, the protrusion 33 elastically rebounds to its free position, thereby removing the frictional engagement between the internal surface of the channel 36 and the shaft 10.

In one embodiment, to enable an interference fit connection the amount of interference between the protrusion 33 and the lower socket 22 less than the radial yield strain of the chosen material, and preferably less than 75% of the radial yield strain. To ensure that an interference fit is achieved, the interference between the protrusion 33 and the lower socket 22 is typically at least 10% of the radial yield strain and preferably greater than 25% of the radial yield strain. Alternatively, other percentages can also be used. For example, provided that the outer surface 31 of protrusion 33 defines a diameter of 0.500 inch, and provided that the body 20 and sleeve 30 are made from a titanium alloy, then the yield strain would be approximately 0.0035 inch. Therefore, the preferred interference would be greater than 0.0009 inch and less than 0.0027 inch.

The frictional engagement between the protrusion 33 and the lower socket 22 defines a longitudinal connection length 29. In one embodiment the connection length is of sufficient length to produce a connection strength that can withstand physiological loads, yet must remain short enough so that assembly loads are not excessive. By way of example and not by limitation, the connection length is generally between 0.020 inch and 0.500 inch, and preferably between 0.040 inch and 0.100 inch. Other ranges can also be used.

To facilitate the relative sliding between the shaft 10, body 20 and sleeve 30, transition surfaces may be included as needed on mating surfaces. As depicted in FIG. 1A, outer surface 31 of the protrusion 33 may have a chamfer 32 serving as a transition between second top end 34 and outer surface 31. Additionally, the bore 26 may include the internal chamfer 23 serving as a transition between first bottom end 25 and the internal surface of the lower socket 22.

An alternate structure of the protrusion 33A and the lower socket 22A is depicted in FIGS. 2A and 2B. Outer surface 31A of protrusion 33A and the inner surface of lower socket 22A are formed into complementary self-locking tapers. Slots 39 descending downward from second top end 34 form the protrusion 33A into a collect-like structure. As the protrusion 33A is advanced into the lower socket 22A, the protrusion is forced inward, creating a frictional engagement between the inner surface of the channel 36 and the shaft 10. Simultaneously, a frictional engagement is created between the outer surface 31A of protrusion 33A and the inner surface of bore 26. The latter frictional engagement is, in essence, a self-locking taper connection. Generally speaking, the self-locking taper would have an included angle in a range between about 2° and about 8°, and preferably the self-locking taper would have an included angle between about 3° and about 6°. Other angles can also be used.

To facilitate the compression between body 20 and sleeve 30, a threaded fastener 40 engages a threaded hole 12 in the third top end 13 of the shaft 10 as depicted in FIGS. 2A–3B. In these embodiments, the shaft 10 includes a shoulder 11 for applying counter compression to the action of the fastener 40. The fastener 40 contacts the first top end of the body 20 and draws the shaft 11 and sleeve 30 into the body 20 to releasably lock the body 20, sleeve 30 and shaft 11 in a fixed relative position.

Another alternate embodiment is depicted in FIGS. 3A and 3B wherein the protrusion 33B includes multiple resilient elements 19. The resilient elements are formed by a series of longitudinal slots 18 through the protrusion 33B. The longitudinal slots may or may not extend to the second top end 34. The longitudinal cross section of the protrusion 33B is in the form of an arch, but could be any geometry which would adequately flex when compressed between two surfaces. The maximal dimension of the outer surface 31B of the protrusion is sized to interfere with the lower socket 22. Upon compressing the protrusion 33B into the lower socket 22, the resilient elements flex to create a frictional engagement between the outer surface 31B of protrusion 33B and the inner surface of bore 26, and simultaneously creating a frictional engagement between the inner surface of the channel 36 and the shaft 10.

Figure 2:
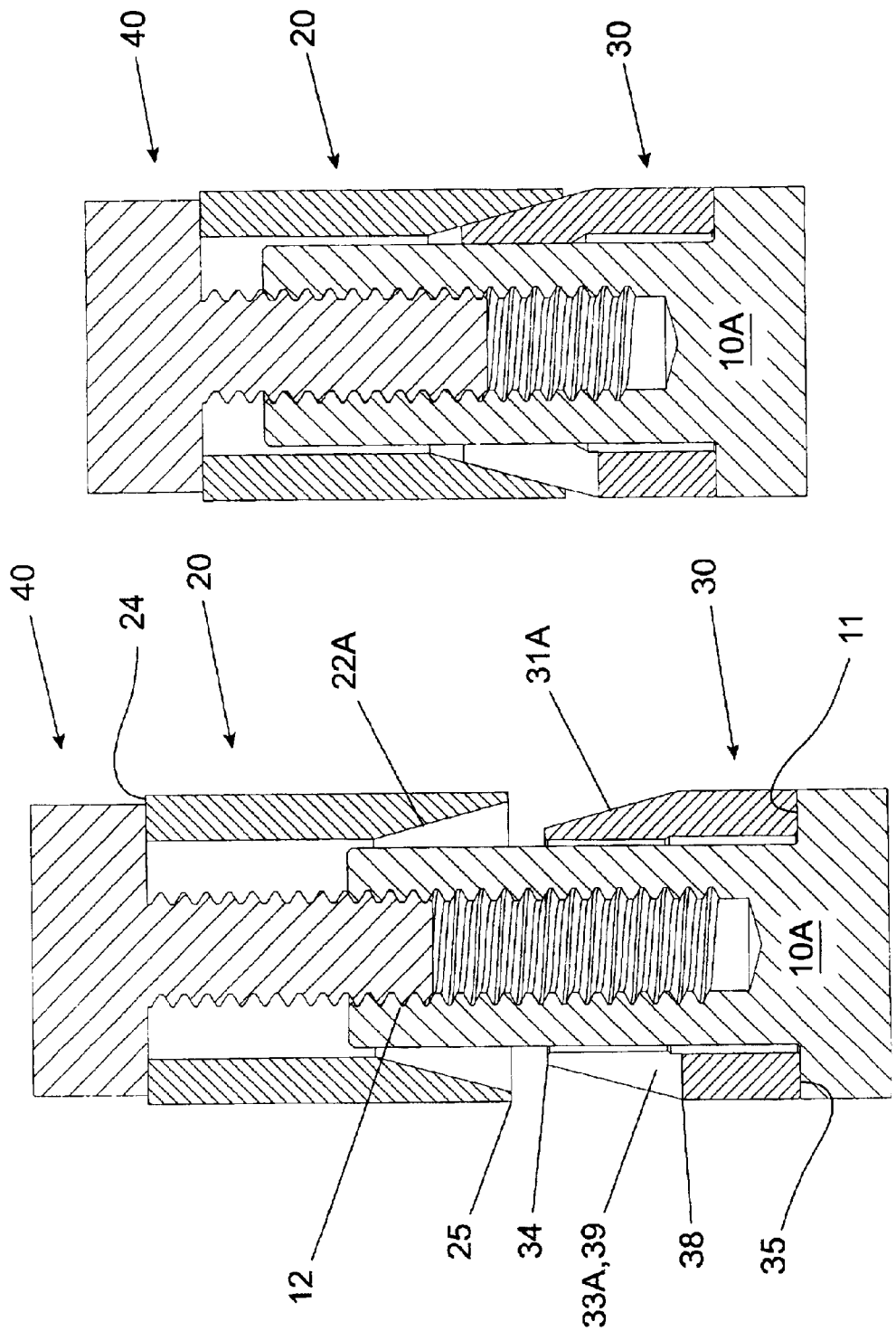
FIG. 2A is a cross sectional view of another embodiment of a tripartite attachment mechanism in a disassembled state.
FIG. 2B is the tripartite attachment mechanism shown in FIG. 2A in an assembled state.
Figure 4:
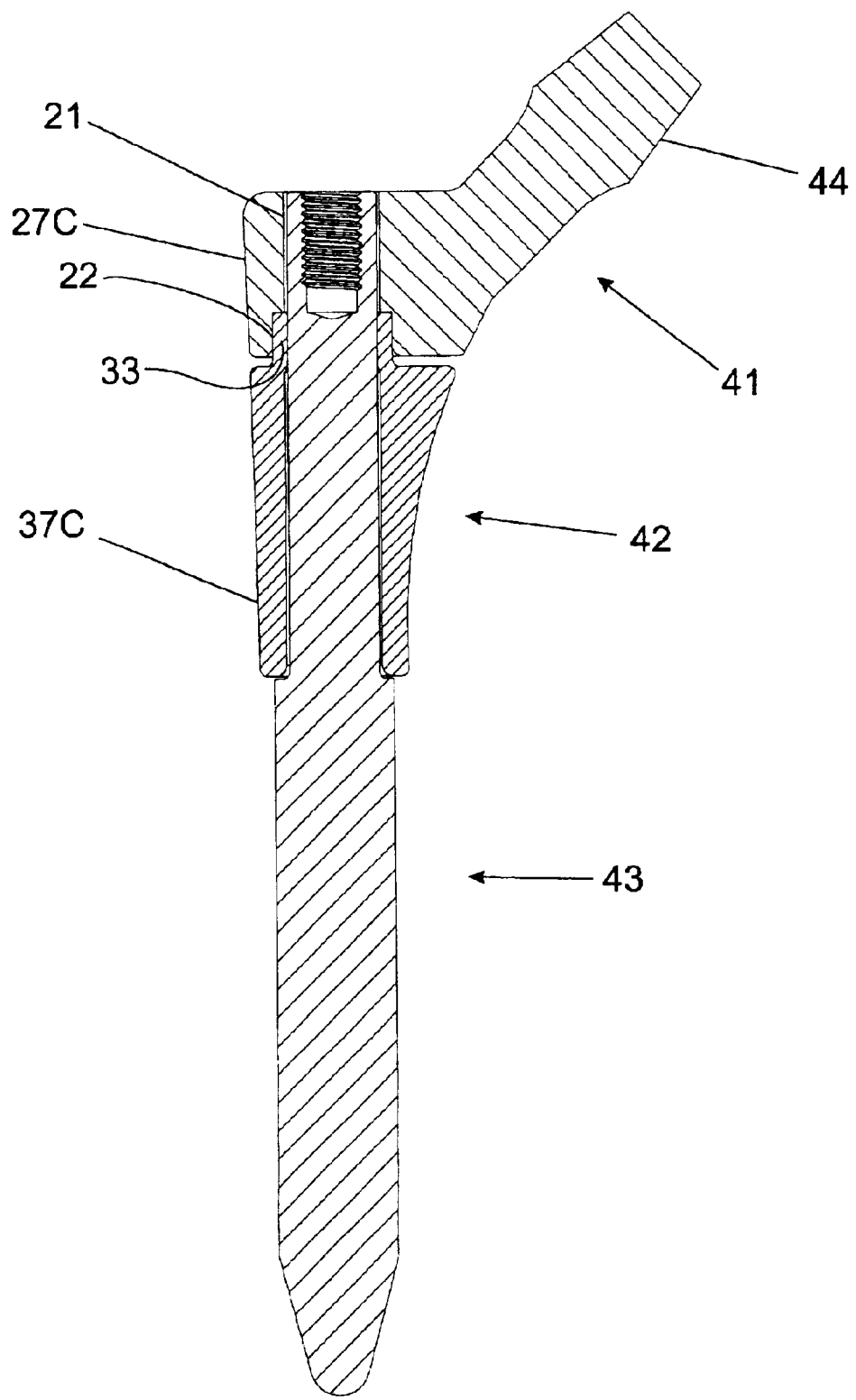
FIG. 4 is a cross sectional view of a modular femoral hip implant having component s connected together by a tripartite attachment mechanism.
Figure 5:
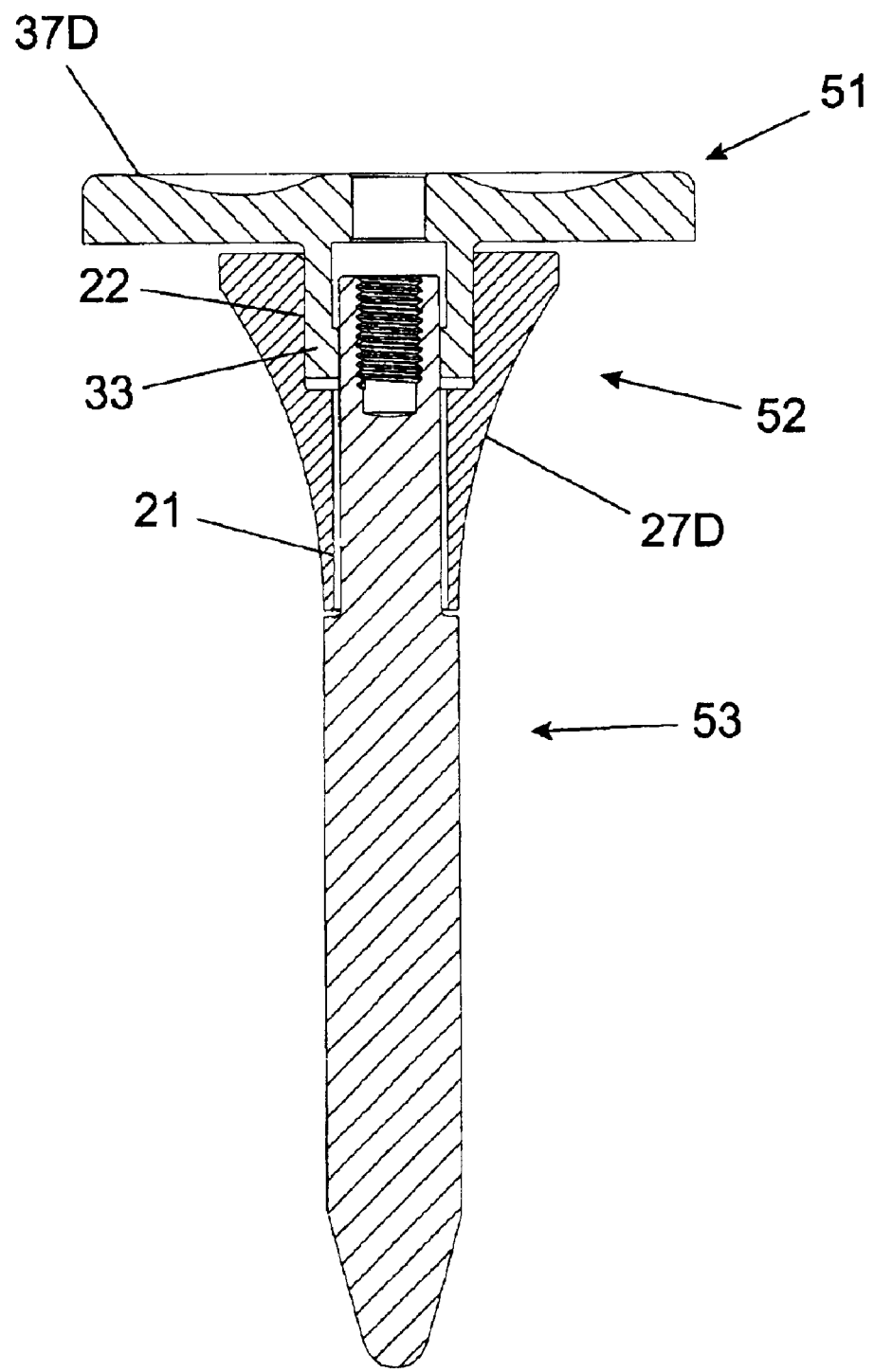
FIG. 5 is a cross sectional view of a modular tibial knee implant having components connected together by a tripartite attachment mechanism.

Depicted in FIG. 4 is a modular femoral hip implant, wherein a prosthetic neck 41 is analogous to the body 20 shown in FIGS. 1–3, a prosthetic body 42 is analogous to the sleeve 30 shown in FIGS. 1–3, and a prosthetic stem 43 is analogous to the shaft 10. The prosthetic neck 41 is adapted to fit into a proximal femur that has a resected femoral head, the prosthetic body 42 is adapted to fit into the top of the resected femur, and the prosthetic stem 42 is designed to fit into an intramedullary canal of a femur. The prosthetic neck 41 has bore 26 with an upper socket 21 and a lower socket 22, and the prosthetic body has protrusion 33. A frustoconical surface 44 is adapted to carry a spherical ball (not shown) adapted to articulate with a prosthetic or natural acetabulum (not shown). It is appreciated that any of the embodiments depicted in FIGS. 1–3 can be substituted to permit secure attachment between prosthetic neck 41, prosthetic body 42, and prosthetic stem 43.

Depicted in FIG. 5 is a modular tibial knee implant, wherein a prosthetic plate 51 is analogous to the sleeve 30 shown in FIGS. 1–3, a prosthetic body 52 is analogous to the body 20 shown in FIGS. 1–3, and the prosthetic stem 53 is analogous to the shaft 10 shown in FIGS. 1–3. The prosthetic plate 51 is designed to fit onto a proximal tibia that has its upper most surface resected, the prosthetic body 52 is adapted to fit into the top of the resected tibia, and the prosthetic stem 52 is designed to fit into an intramedullary canal of the tibia. The prosthetic neck 51 has protrusion 33, and the prosthetic body has bore 26 with an upper socket 21 and a lower socket 22. It is appreciated that any of the embodiments depicted in FIGS. 1–3 can be substituted to permit secure attachment between prosthetic plate 51, prosthetic body 52, and prosthetic stem 53.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An attachment mechanism for securely connecting components of a modular prosthesis, the attachment mechanism comprising:

a body comprising a first top end, a first bottom end, and a first internal surface bounding a bore extending between the first top end and first bottom end, the bore comprising a first socket formed at the first bottom end of the body, the body further having a first external prosthetic surface;

a sleeve comprising a second top end, a second bottom end, and a second internal surface bounding a channel extending between the second top end and the second bottom end, the sleeve further comprising an external surface extending between the second top end and the second bottom end with a shoulder being formed thereon, the external surface of the sleeve comprising a second external prosthetic surface extending between the shoulder and the second bottom end, and an outer engagement surface extending between the shoulder and the second top end, a portion of the sleeve extending between the shoulder and the second top end forming a tubular protrusion at least a portion of the outer engagement surface and the second internal surface being formed on the tubular protrusion; and a shaft received within the bore of the body and the channel of the sleeve, an engaging portion of the shaft being disposed within and being smaller than a portion of the channel bounded by the tubular protrusion when the tubular protrusion is in a relaxed position, the tubular protrusion of the sleeve being pressed from the first bottom end of the body into the first socket so that the tubular protrusion is retained at the first bottom end of the body and forms an interference fit within the first socket of the body, the interference fit causing at least a portion of the first internal surface of the body to bias in secure frictional engagement with at least a portion of the outer engagement surface of the tubular protrusion of the sleeve and causing at least a portion of the second internal surface of the tubular protrusion of the sleeve to radially inwardly constrict in an elastic deformation so as to bias in secure frictional engagement with the engaging portion of the shaft, the interference fit between the tubular protrusion and the body being the sole mechanical connection between the sleeve and the body.

2. The attachment mechanism according to claim 1, wherein the tubular protrusion is a solid tube.

3. The attachment mechanism according to claim 1, wherein the tubular protrusion is a collet.

4. The attachment mechanism of claim 3, wherein a portion of the outer engagement surface and a portion of the first internal surface define complementary self-locking tapers.

5. The attachment mechanism according to claim 1, wherein the tubular protrusion includes a resilient element.

6. The attachment mechanism of claim 1, wherein a portion of the outer engagement surface and a portion of the first internal surface define complementary self-locking tapers.

7. The attachment mechanism according to claim 1, wherein the first socket and the tubular protrusion each have a substantially cylindrical configuration when in a relaxed state.

8. The attachment mechanism accord in to claim 1, wherein the bore of the body further comprises a second socket formed at or toward the first top end of the body.

9. The attachment mechanism according to claim 8, further comprising an annular shoulder radially inwardly projecting from the first internal surface of the body between the first socket and the second socket.

10. The attachment mechanism according to claim 1, further comprising an annular shoulder formed on the second internal surface of the sleeve.

11. The attachment mechanism according to claim 1, wherein the second top end of the sleeve biases against a shoulder formed on the internal surface of the body.

12. The attachment mechanism according to claim 1, wherein the secure fictional engagement between the tubular protrusion and the shaft is the sole mechanical connection connecting the sleeve to the shaft.

13. The attachment mechanism according to claim 1, wherein the engaging portion of the shaft and the internal surface of the tubular protrusion each have a substantially cylindrical configuration when in a relaxed state.

14. An attachment mechanism for securely connecting components of a modular prosthesis, the attachment mechanism comprising:

a body comprising a first top end, a first bottom end, and a first internal surface bounding a bore extending between the first top end and first bottom and, the bore comprising an upper socket and a lower socket, the body further having an external prosthetic surface;

a sleeve comprising a second top end, a second bottom end, and a second internal surface bounding a channel extending between the second top end and the second bottom end, the sleeve further comprising an external surface extending between the second top end and the second bottom end with a shoulder being formed thereon, the external surface of the sleeve comprising an external prosthetic surface extending between the shoulder and the second bottom end, and an outer engagement surface extending between the shoulder and the second top end, a portion of the sleeve extending between the shoulder and the second top end forming a tubular protrusion; and a shaft sized to be slidingly received within the bore of the body and the channel of the sleeve;

whereby when the shaft is position in both the upper socket of the bore of the body and the channel of the sleeve, pressing the tubular protrusion of the sleeve into the lower socket of the body forms an interference fit that causes the tubular protrusion to radially inwardly elastically deflect such that at least a portion of the second internal surface of the sleeve biases in secure frictional engagement with the shaft, thereby releasably locking the body, sleeve and shaft in a fixed relative position.

15. The attachment mechanism according to claim 14, wherein the interference fit is between 0.0005 inch and 0.01 inch.

16. The attachment mechanism according to claim 14, wherein the interference fit is between 0.001 inch and 0.003 inch.

17. The attachment mechanism according to claims 14, wherein the frictional biasing between the first internal surface of the body and the outer engagement surface of the sleeve define a longitudinal contact length which is between 0.02 inch and 0.5 inch.

18. The attachment mechanism according to claim 14, wherein the frictional biasing between the first internal surface of the body and the outer engagement surface of the sleeve define a longitudinal contact length which is between 0.04 inch and 0.1 inch.

19. The attachment mechanism according to claim 14, wherein the tubular protrusion is a solid tube.

20. The attachment mechanism according to claim 14, wherein the tubular protrusion is a collet.

21. The attachment mechanism according to claim 14, wherein the tubular protrusion includes a resilient element.

22. The attachment mechanism of claim 14, wherein a portion of the outer engagement surface and a portion of the first internal surface define complementary self-locking tapers.

23. The attachment mechanism according to claim 14, wherein the interference fit between the tubular protrusion and the body is the sole mechanical connection between the sleeve and the body.

24. The attachment mechanism according to claim 14, wherein the secure frictional engagement between the tubular protrusion and the shaft is the sole mechanical connection connecting the sleeve to the shaft.

25. The attachment mechanism according to claim 14, wherein the lower socket of the body has a larger diameter than the upper socket of the body.

* * * * *

UNITED STATES PATENT AND TRADEMARK OFFICE
CERTIFICATE OF CORRECTION

PATENT NO. : 6,902,583 B2  Page 1 of 1
APPLICATION NO. : 10/132669
DATED : June 7, 2005
INVENTOR(S) : Daniel E. Gerbec It is certified that error appears in the above-identified patent and that said Letters Patent is hereby corrected as shown below:

Column 6, Line 8 (Claim 12) DELETE "fictional" which follows "bottom" and ADD --frictional--

Col. 6 Line 20 6.20 (Claim 14) DELETE "and" which follows "bottom" and ADD --end--

Col. 6 Line 38 6.38 (claim 14) DELETE "position" abd ADD --positioned--

Col. 6 Line 54 6.54 (Claim 17) DELETE "claims" and ADD --claim--

Signed and Sealed this

Nineteenth Day of December, 2006

JON W. DUDAS
*Director of the United States Patent and Trademark Office*